(12) United States Patent
Uenaka et al.

(10) Patent No.: US 6,506,903 B1
(45) Date of Patent: Jan. 14, 2003

(54) PROCESS FOR PRODUCING 4-THIAZOLYLMETHYL DERIVATIVE

(75) Inventors: Masaaki Uenaka, Osaka (JP); Masahiko Nagai, Osaka (JP); Naotake Kobayashi, Shiga-ken (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/622,441

(22) PCT Filed: Mar. 1, 1999

(86) PCT No.: PCT/JP99/00975
§ 371 (c)(1),
(2), (4) Date: Aug. 17, 2000

(87) PCT Pub. No.: WO99/45000
PCT Pub. Date: Sep. 10, 1999

(30) Foreign Application Priority Data

Mar. 29, 1908 (JP) .............................................. 10-49259

(51) Int. Cl.⁷ ............................................ C07D 277/22
(52) U.S. Cl. ....................................... 548/204; 548/202
(58) Field of Search ................................ 548/204, 202

(56) References Cited

U.S. PATENT DOCUMENTS

| | | | |
|---|---|---|---|
| 5,275,950 A | 1/1994 | Dickman et al. | |
| 5,459,274 A | 10/1995 | Lee et al. | |
| 5,622,973 A | 4/1997 | Morriello et al. | |

FOREIGN PATENT DOCUMENTS

| | | |
|---|---|---|
| EP | 0302389 A2 | 2/1989 |
| EP | 0933379 A1 | 8/1999 |
| JP | A7304768 | 11/1995 |

OTHER PUBLICATIONS

Rubina, Khim. Geterotsikl. Soedin. (4) 543–6 1989 Abstract Only.*
Dauphin, G. et al, Synthesis, 149, Mar. 1973, pp. 149–151.
Scheibye, S. et al, Bull. Soc. Chim. Belg., 87, 3, pp. 229–238, 1978.

Hsiao, C. N. et al, Synth. Commun., 20, 22, pp. 3507–3517, 1990.

Nishi, T. et al, Chem. Pharm. Bull., 38, 1, pp. 103–109, 1990.

Rubina et al., *Chemistry of Heterocyclic Compounds*, (English Translation), vol. 25, No. 4, pp. 454–457 (1989) XP001064498.

Caldwell et al., *Journal of the American Chemical Society*, vol. 73, No. 6, pp. 2935–2936 (Jun. 6, 1951) XP002193865.

Watanabe et al., *Bulletin of the Chemical Society of Japan*, vol. 39, No. 11, pp. 2473–2476 (Nov. 1966) XP002193866.

Nishi et al., *Chemical & Pharmaceutical Bulletin*, vol. 38, No. 1, pp. 103–109 (Jan. 1990) XP002193867.

Hsiao et al., *Synthetic Communications*, vol. 20, No. 22, pp. 3507–3517 (1990) XP001064494.

Lopyrev et al., Zh. Onshch. Khim., vol. 66, No. 8, pp. 1374–1376 (1996).

* cited by examiner

*Primary Examiner*—Robert Gerstl
(74) *Attorney, Agent, or Firm*—Birch, Stewart, Kolasch & Birch, LLP

(57) ABSTRACT

A process for the production of 4-thiazolylmethyl derivatives are provided. A process for the production of the compound represented by the formula (I):

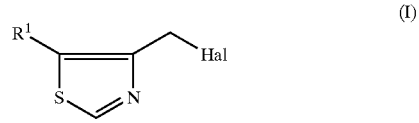

wherein $R^1$ is hydrogen or halogen and Hal is halogen, which comprises reacting 4-methylthiazole with N-halosuccinimide in a solvent in the presence of a radical initiator.

14 Claims, No Drawings

PROCESS FOR PRODUCING 4-THIAZOLYLMETHYL DERIVATIVE

This application is the national phase under 35 U.S.C. §371 of PCT International Application No. PCT/JP99/00975 which has an International filing date of Mar. 1, 1999, which designated the United States of America.

TECHNICAL FIELD

This invention relates to a process for the production of a thiazolyl alanine derivative which is a nonnatural amino acid by a simple and economical method.

BACKGROUND ART

A thiazolyl alanine derivative such as 4-halomethylthiazole, 3-(4-thiazole) alanine, or the like is an important intermediate for the production of ES 6864 described in Synth. Commun., 20, 22, 3570 (1990) as a renin inhibitor and a TRH (thyrotropin-releasing hormone) derivative described in WO 98/08867 which is represented by the the formula (V):

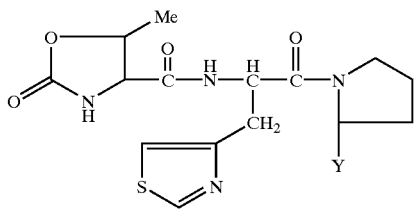

(V)

wherein Y is optionally substituted alkyl. Further, a thiazolyl alanine derivative, a nonnatural amino acid, is useful as a tool of the combinatorial chemistry.

As a process for the production of a thiazolyl alanine derivative, two methods shown below have already been known. The first method consists of the following 3 steps:

(1) a reaction of formaldehyde with phosphorus pentoxide to give thioformamide (Synthesis, 149 (1973)) or (1') a reaction of formaldehyde with Lawesson's reagent to give thioformamide (Bull. Soc. Chim. Belg., 87, 3, 229 (1978)), (2) a reaction of thioformamide with 1,3-dichloro-2-prooanone to give 4-chloromethylthiazole, and (3) alkylation, decarboxylation, and optical resolution to give optically active 3-(4-thiazole)alanine (Synth. Commun., 20, 22, 3507(1990) and Chem. Pharm. Bull., 38, 1, 103(1990)).

Step (1) has some problems such as difficulty of waste disposal, because insoluble products in the reaction mixture have bad smell peculiar to sulfur compounds and do not dissolve in water and any organic solvent except for dimethylsulfoxide. The step (1') is not appropriate for large scale synthesis because Lawesson's reagent is expensive. Further, as regards the step (2), 1,3-dichloro-2-propanone has a tearing property.

The second method for the production of a thiazolyl alanine derivative consists of the following 2 steps:

(1) a reaction of diethyl (3-bromo-2-oxo-propyl)acetamide malonate with thioformamide to give diethyl (4-thiazolylmethyl)acetamide malonate and (2) hydrolysis, decarboxylation, and optical resolution using esterase to give optically active 3-(4-thiazole) alanine (U.S. Pat. No. 5,275,950).

In this method, use of thioformamide is also necessary as described in the above method.

DISCLOSURE OF INVENTION

The object of the present invention is to provide a process for the simple and economical production of a thiazolyl alanine derivative which is a nonnatural amino acid. The thiazolyl alanine derivative is useful as an intermediate of medicaments and a tool of the combinatorial chemistry.

The present inventors have found a process, using 4-methylthiazole as a starting material, for the production of a thiazolyl alanine derivative, which is suitable for large scale synthesis.

This invention relates to A) a process for the production of a compound represented by the formula (I):

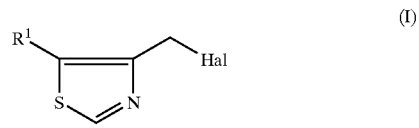

(I)

wherein $R^1$ is hydrogen or halogen and Hal is halogen, which comprises reacting 4-methylthiazole with N-halosuccinimide in a solvent in the presence of a radical initiator.

In more detail, the invention relates to B) a process for the production of a compound represented by the formula (II):

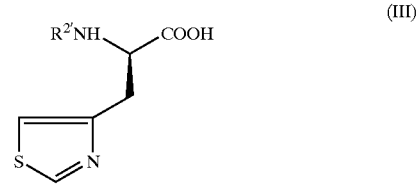

(III)

wherein $R^{2'}$ is hydrogen or an amino protective group, or the formula (IV):

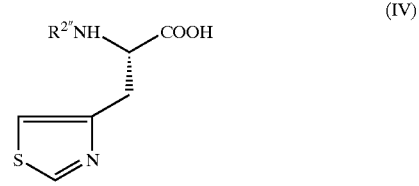

(IV)

wherein $R^{2''}$ is different from $R^{2'}$ and hydrogen or an amino protective group, which comprises, (a) preparing a compound represented by the formula (I):

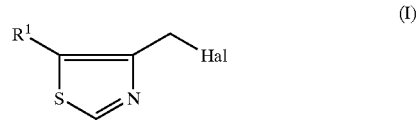

(I)

wherein $R^1$ is hydrogen or halogen and Hal is halogen, by reacting 4-methylthiazole with N-halosuccinimide in a solvent in the presence of a radical initiator, (b) preparing a compound represented by the formula (I):

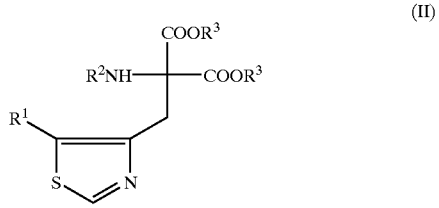

(II)

wherein $R^1$ is as defined above, $R^2$ is an amino protective group, and $R^3$ is lower alkyl, by reacting a compound represented by the formula (I) with $R^2NHCH(COOR^3)_2$, wherein $R^2$ and $R^3$ are as defined above, in the presence of a base, (c) dehalogenating the compound represented by the formula (II) when $R^1$ is halogen, and, (d) preparing a compound represented by the formula (III) by subjecting the compound represented by the formula (II) to hydrolysis, decarboxylation, and optical resolution.

C) A process for the production of a compound represented by the formula (V):

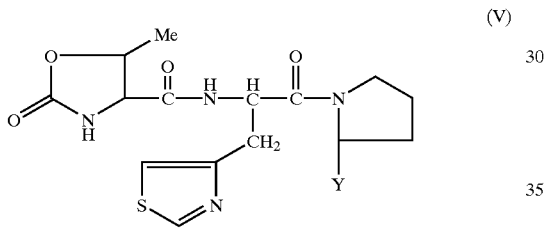

(V)

wherein Y is optionally substituted alkyl, which comprises subjecting a compound represented by the formula (III) or (IV) to a peptide bond formation reaction.

D) A process as described in any one of A) to C) wherein the solvent is chlorobenzene, the radical initiator is 2,2-azobisisobutyronitrile, and N-halosuccinimide is N-chlorosuccinimide.

E) A process as described in any one of A) to C) wherein the solvent is carbon tetrachloride, the radical initiator is 2,2-azobisisobutyronitrile, and N-halosuccinimide is N-bromosuccinimide.

F) A process as described in any one of A) to C) wherein the solvent is carbon tetrachloride, the radical initiator is benzoyl peroxide, and N-halosuccinimide is N-bromosuccinimide.

G) A process for the production of 4-chloromethylthiazole comprising, (e) reacting 4-methylthiazole with N-chlorosuccinimide in chlorobenzene in the presence of 2,2-azobisisobutyronitrile and (f) treating the compound obtained in the step (e) with hydrochloric acid to give the corresponding hydrochloride, followed by decarboxylation.

H) A process for the production of a compound represented by the formula (III):

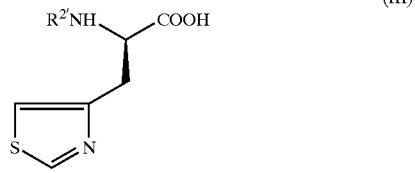

(III)

wherein $R^{2'}$ is as defined above, or the formula (IV):

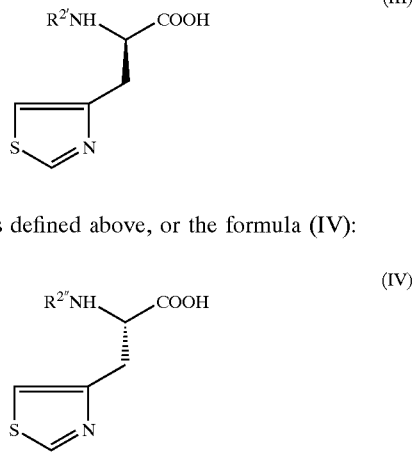

(IV)

wherein $R^{2''}$ is as defined above, which comprises, (g) preparing 5-bromo-4-bromomethylthiazole by reacting 4-methylthiazole with N-bromosuccinimide in carbon tetrachloride in the presence of benzoyl peroxide, (h) preparing a compound represented by the formula (VI):

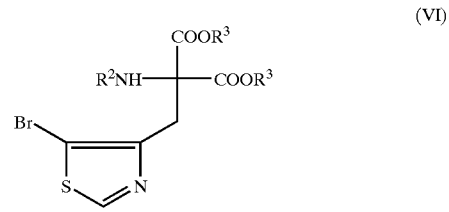

(VI)

wherein $R^2$ and $R^3$ are as defined above, by reacting 5-bromo-4-bromomethylthiazole with $R^2NHCH(COOR^3)_2$, wherein $R^2$ and $R^3$ are as defined above in the presence of a base, and (i) subjecting the compound represented by the formula (VI) to dehalogenation, hydrolysis, decarboxylation, and optical resolution.

The above steps (d) and (i) are preferred to be carried out successively in order of hydrolysis, decarboxylation, and optical resolution.

The peptide bond formation reaction in the step C) is preferred to be carried out twice in appropriate order.

The term "halogen" herein used includes fluoro, chloro, bromo, and iodo. Preferred are chloro and bromo.

The term "lower alkyl" herein used includes straight or branched $C_1$–$C_6$ chain alkyl. Examples of lower alkyl are methyl, ethyl, n-propyl, iso-propyl, n-butyl, sec-butyl, iso-butyl, t-butyl, and the like. Preferably, methyl and ethyl are exemplified.

Examples of "an amino protective group" are acetyl and n-butyryl.

The term "optionally substituted alkyl" herein used includes $C_1$–$C_6$ straight or branched chain alkyl or $C_3$–$C_8$ cycloalkyl which is optionally substituted at any possible position(s) with one or more substituents, for example, hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, carbamoyl, alkyloxycarbonyl (e.g., methoxycarbonyl and ethoxycarbonyl), aryloxycarbonyl (e.g., phenyloxycarbonyl), nitro, cyano, $SO_pR^A$ (p is an integer of 1 to 3, and $R^A$ is hydrogen or alkyl), $PO(OH)_2$ or $P(O)OH$ each is optionally substituted with alkyl, substituted or unsubstituted amino (e.g., methylamino, dimethylamino, and carbamoylamino), optionally substituted aryl (e.g., phenyl and tolyl), optionally substituted heteroaryl, an optionally substituted non-aromatic heterocyclic group, aryloxy, acyloxy, acyloxycarbonyl, alkylcarbonyl, non-aromatic heterocyclic carbonyl, heterocyclic imino, hydrazino, hydroxyamino, alkyloxyamino, formyl, and the lile. Examples of optionally substituted alkyl are methyl, ethyl, n-propyl, iso-propyl, n-butyl, iso-butyl, sec-butyl, tert-butyl, cyclopropyl, cyclopentyl, cyclohexyl, benzyl, hydroxymethyl, tert-butylcarbonyloxymethyl, morpholinomethyl, piperidinomethyl, N-methyl-1-piperazinylmethyl, ethylcarbonylmethyl, morpholinocarbonylmethyl, acetyloxymethyl, and the like. As a preferable substituent, phenyl, hydroxy, alkylcarbonyloxy, morpholino, piperidino, N-alkyl substituted piperazinyl, alkylcarbonyl, morpholinocarbonyl, and acyloxy are exemplified.

Examples of "solvent" are carbon tetrachloride, tetrahydrofuran, acetonitrile, 1,4-dioxane, cyclohexane, sulfolane, chlorobenzene, bromobenzene, trifluoromethylbenzene. Preferably, carbon tetrachloride, chlorobenzene, trifluoromethylbenzene are exemplified.

Examples of "radical initiator" are 2,2-azobisisobutyronitrile (AIBN) and benzoyl peroxide (BPO).

BEST MODE FOR CARRYING OUT THE INVENTION

The present process is described as the following schemes and explained in more detail.

Production Example 1

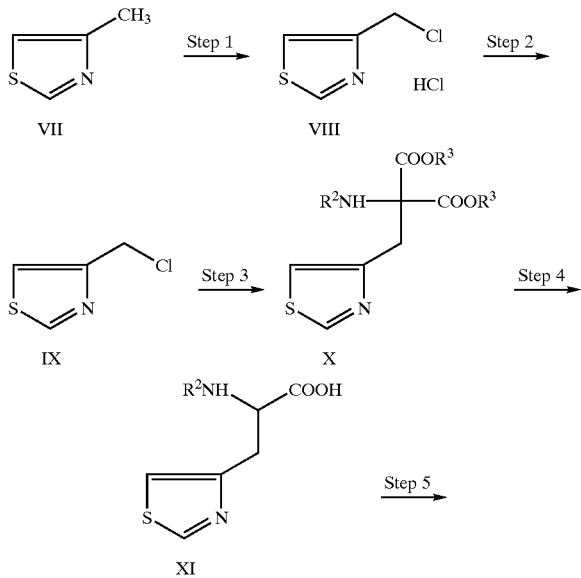

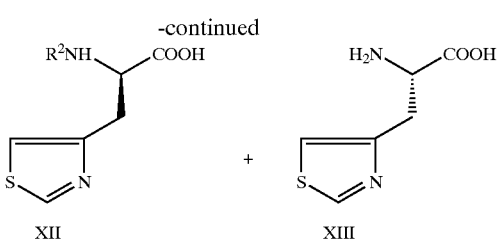

wherein $R^2$ and $R^3$ are as defined above.

Step 1-1

Compound (VII), a commercially available chemical reagent is dissolved in a solvent such as carbon tetrachloride, tetrahydrofuran, acetonitrile, 1,4-dioxane, cyclohexene, sulfolane, chlorobenzene, bromobenzene, trifluoromethylbenzene, preferably, carbon tetrachloride, chlorobenzene, and the like. To this solution are added 0.9 to 1.5 eq., preferably 1.0 to 1.2 eq. of N-chlorosuccinimide and 0.05 to 0.2 eq., preferably 0.05 to 0.1 eq. of AIBN or BPO at 60 to 160° C., preferably at reflux and the resulting mixture is stirred for 5 to 30 min., preferably 10 to 20 min. Usual after-treatment gives 4-chrolomethylthiazole.

Step 1-2

The compound obtained in the above step is treated with hydrochloric acid to give compound (VIII). For example, this reaction is carried out as follows: the starting material is dissolved in a solvent such as ethyl acetate, toluene, or the like, then 1 to 4 N hydrochloric acid in ethyl acetate etc. is added to the mixture, and the precipitated crystalline is collected.

Step 2 (Desalting reaction)

To a solution of compound (VIII) in water, and was added an organic solvent such as toluene, ethyl acetate or the like, then sodium hydrogencarbonate, sodium carbonate, etc. is added to the mixture to give the compound (IX).

Step 3

To a solution of sodium methoxide (1.0 to 1.2 eq., preferably 1.0 to 1.1 eq.) in methanol or a solution of sodium ethoxide (1.0 to 1.2 eq., preferably 1.0 to 1.1 eq.) in ethanol is added $R^2$ $NHCH(COOR^3)_2$ (0.8 to 1.2 eq., preferably 0.9 to 1.0 eq.), wherein $R^2$ and $R^3$ are as defined above, and the mixture is stirred for 1 to 5 h, preferably 1.5 to 3 h at 50 to 100° C., preferably at reflux. Then, to the mixture is added a solution of compound (IX) in methanol or ethanol at 25 to 70° C., preferably 50 to 60° C. and the resulting mixture is stirred for 1 to 6 h, preferably 2 to 4 h at the same temperature. Usual after-treatment gives compound (X).

Step 4 (Hydrolysis and decarboxylation)

This step is carried out under usual conditions for hydrolysis and decarboxylation. For example, compound (X) is suspended in 1 to 4 N sodium hydroxide aq. and the mixture is stirred for 0.5 to 3 h, preferably 1 to 2 h at 25 to 100° C., preferably 25 to 50° C. (hydrolysis). To this solution is added conc. hydrochloric acid for adjusting the pH to 3 to 4, preferably 3.5 and the mixture is stirred for 1 to 5 h, preferably 2 to 4 h at 70 to 100° C., preferably 100° C. while keeping the pH about 4. Usual after-treatment gives compound (XI).

Step 5 (Optical Resolution)

This step is the hydrolysis of the N-acyl group of the L-isomer or D-isomer, using an enzyme such as acylase. The selection of the enzyme leads to obtain an amino acid which has a desired configuration (Agric. Biol. Chem., 44, 1089–1095 (1980) and "Kikankagakusousetsu", No. 6 (1989), 97–99, Chemical Society of Japan). The purification is carried out more easily by protecting the amino group of the resulting amino acid with a protective group such as Boc.

Production Example 2

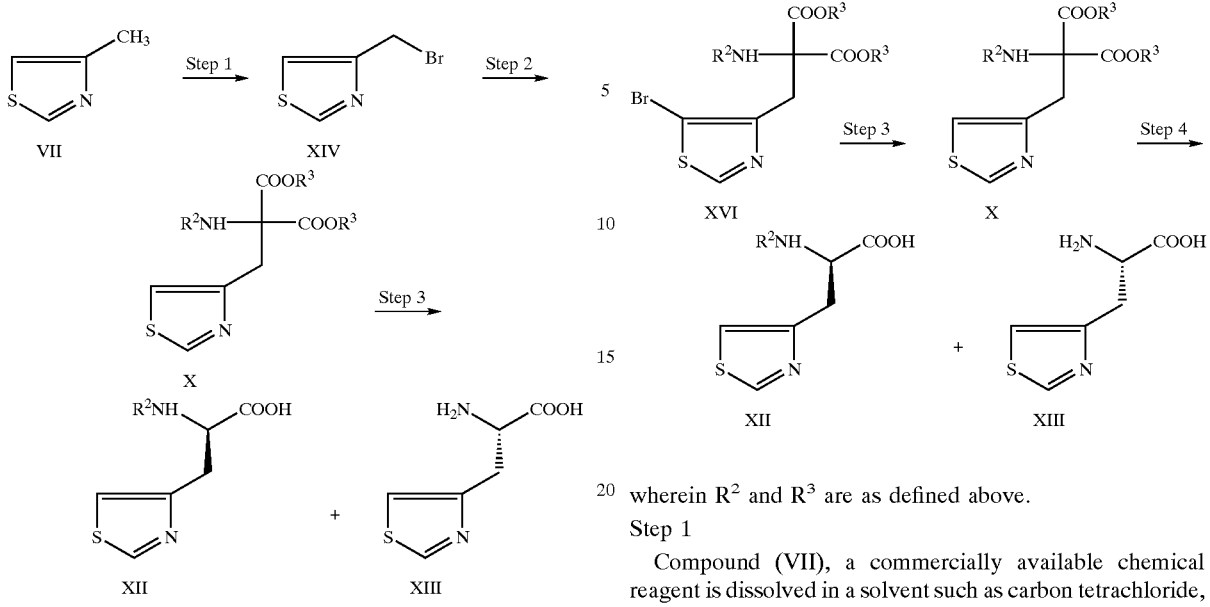

wherein $R^2$ and $R^3$ are as defined above.

Step 1

Compound (VII), a commercially available chemical reagent is dissolved in a solvent such as carbon tetrachloride, tetrahydrofuran, acetonitrile, 1,4-dioxane, cyclohexene, sulfolane, chlorobenzene, bromobenzene, trifluoromethylbenzene, preferably, carbon tetrachloride, chlorobenzene, or the like. To this solution are added 0.5 to 1.5 eq., preferably 0.8 to 0.9 eq. of N-bromosuccinimide and 0.02 to 0.2 eq., preferably 0.05 to 0.1 eq. of AIBN at 60 to 160° C., preferably at reflux and the resulting mixture is stirred for 5 to 30 min., preferably 10 to 20 min. Usual after-treatment gives compound (XIV).

Step 2

To a solution of sodium methoxide (0.7 to 1.2 eq., preferably 0.8 to 1.1 eq.) in methanol or a solution of sodium ethoxide (0.7 to 1.2 eq., preferably 0.8 to 1.1 eq.) in ethanol is added $R^2$ NHCH(COOR$^3$)$^2$ (0.7 to 1.2 eq., preferably 0.8 to 1.0 eq.), wherein $R^2$ and $R^3$ are as defined above, and the resulting mixture is stirred for 1 to 5 h, preferably 1.5 to 3 h at 50 to 80° C., preferably at reflux. Then, to the mixture is added a solution of compound (XIV) in methanol or ethanol at 25 to 70° C., preferably 50 to 60° C. and the resulting mixture is stirred for 1 to 6 h, preferably 2 to 4 h at the same temperature. Usual after-treatment gives compound (X).

Step 3

This step may be carried out according to Production Example 1—Step 4 to 5.

Production Example 3

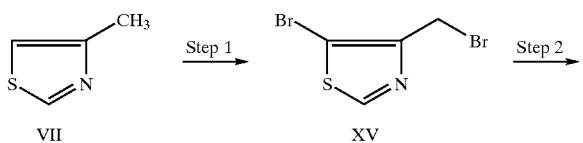

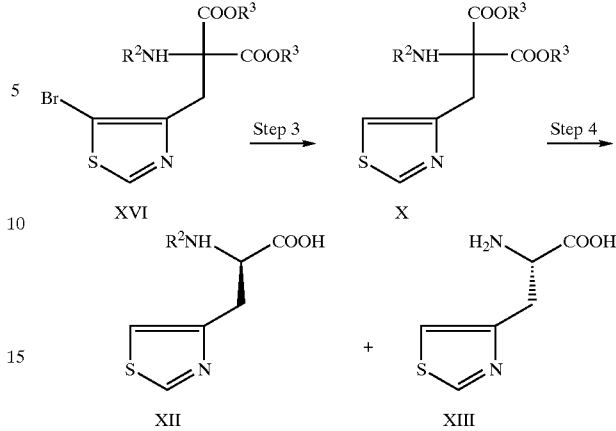

wherein $R^2$ and $R^3$ are as defined above.

Step 1

Compound (VII), a commercially available chemical reagent is dissolved in a solvent such as carbon tetrachloride, tetrahydrofuran, acetonitrile, 1,4-dioxane, cyclohexene, sulfolane, chlorobenzene, bromobenzene, trifluoromethylbenzene, preferably, carbon tetrachloride, chlorobenzene, or the like. To this solution are added 1.8 to 3.0 eq., preferably 2.0 to 2.5 eq. of N-bromosuccinimide and 0.02 to 0.5 eq., preferably 0.2 to 0.3 eq. of BPO at 60 to 160° C., preferably at reflux and the resulting mixture is stirred for 5 to 30 min., preferably 10 to 20 min. Usual after-treatment gives compound (XV).

Step 2

To a solution of sodium methoxide (0.8 to 1.5 eq., preferably 1.0 to 1.2 eq.) in methanol or a solution of sodium ethoxide (0.8 to 1.5 eq., preferably 1.0 to 1.2 eq.) in ethanol is added $R^2$ NHCH(COOR$^3$)$_2$ (0.8 to 1.5 eq., preferably 0.8 to 1.0 eq.), wherein $R^2$ and $R^3$ are as defined above and the resulting mixture is stirred for 1 to 5 h, preferably 1.5 to 3 h at 50 to 80° C., preferably at reflux. Then, to the mixture is added a solution of compound (XV) in methanol or ethanol at 25 to 80° C., preferably 50 to 60° C., and the resulting mixture is stirred for 1 to 6 h, preferably 2 to 4 h at the same temperature. Usual after-treatment gives compound (XVI).

Step 3 (Dehalogenation)

This step is able to be carried out by usual dehalogenation. For example, to a solution of compound (XVI) in a solvent such as methanol, ethanol, ethyl acetate, acetic acid, or the like, preferably methanol, is added a catalyst such as Pd—C, PtO$_2$, Rh—Al$_2$O$_3$, Raney nickel, or the like, preferably Pd—C and the resulting mixture is hydrogenated for 1 to 5 h, preferably 2 to 3 h, at 0 to 100° C., preferably 20 to 30° C. under 1 to 3 atm., preferably 2 to 3 atm.

Step 4

This step is able to be carried out in a manner similar to that described in Production Example 1—Step 4 to 5.

Production Example 4

The compound (V) is synthesized through two peptide bond formation reactions. For example, the synthesis method of the compound (V') using the compound (VIII) which is synthesized by the above method is shown below.

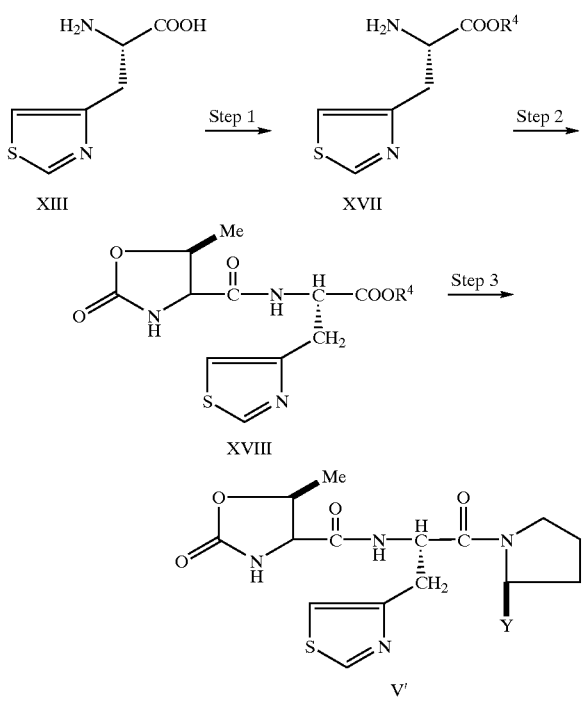

wherein R⁴ is a carboxy protective group and Y is as defined above.

Step 1 (Protection of carboxy)

The carboxy group of compound (XIII) obtained in Production Examples 1 to 3 is protected as ester such as methyl ester, benzyl ester, t-butyl ester, diphenylmethyl ester, or the like protective Groups in Organic Synthesis, Theodora W. Green (John Wiley & Sons)). For example, when the carboxy group is protected as diphenylmethyl ester, compound (XIII) is dissolved in a mixed solvent of alcohol solvent such as methanol, ethanol, or the like and a solvent such as tetrahydrofuran, dioxane, or the like. To the mixture is added dropwise 1 to 3 eq., preferably 1 to 2 eq. of diphenyldiazomethane over 10 min to 1 h, preferably 20 to 40 min at 0 to 50° C., preferably 20 to 40° C. and the resulting mixture is stirred for 30 min to 3 h, preferably 1 to 2 h at the same temperature. Usual after-treatment gives compound (XVII).

Step 2 (Peptide bond formation reaction)

This reaction is carried out in accordance with a usual peptide bond formation reaction described in "Peptide Synthesis", Nobuo Izumiya, Maruzen or the like.

As a usual peptide bond formation reaction, exemplified are the method using a condensing agent such as N,N-dicyclohexylcarbodiimide (DCC) or the like, the azide method, the acid chloride method, the acid anhydride method, the activated ester method, or the like. When the starting material has a substituent (e.g., amino, carboxy, and hydroxy) interfering with this peptide bond formation reaction, the substituent may be protected in advance according to the method of "Protective Groups in Organic Synthesis" Theodora W. Green (John Wiley & Sons), and then deprotected at an appropriate step. For example, compound (XVII) and (R)-(+)-2-methylpyrrolidine hydrochloride which is synthesized by the method described in Tetrahedron, 27, 2599 (1971) are dissolved in a solvent such as N,N-dimethylformamide, tetrahydrofuran, acetonitrile, or the like and to this solution are added a base such as triethylamine or the like and a solution of dicyclohexylcarbodiimide (DCC) in N,N-dimethylformamide at −10 to 10° C., preferably under ice-cooling. 1-Hydroxybenzotriazole may be added to the reaction mixture, if necessary. The resulting mixture is stirred for 1 h to 1 day, preferably 5 to 10 h at 10 to 50° C., preferably 20 to 30° C. Usual after-treatment gives to give compound (XVIII).

Step 3 (Deprotection of R⁴ and Peptide Bond Formation Reaction)

This step may be carried out by a usual deprotection reaction in accordance with the method described in Protective Groups in Organic Synthesis, Theodora W. Green (John Wiley & Sons). For example, when R⁵ is diphenylmethyl, anisole and trifluoroacetic acid are added to compound (XVIII) at −10 to 10° C., preferably under ice-cooling and the mixture is stirred for 5 to 30 min, preferably 10 to 20 min at the same temperature. The resulting mixture is warmed to 20 to 40° C. and stirred for 1 to 4 h, preferably 2 to 3 h. Usual after-treatment gives the deprotected compound.

This deprotected compound is reacted with a pyrrolidine derivative in a peptide bond formation reaction according to the above Step 2 to give compound (V').

Production Example 5

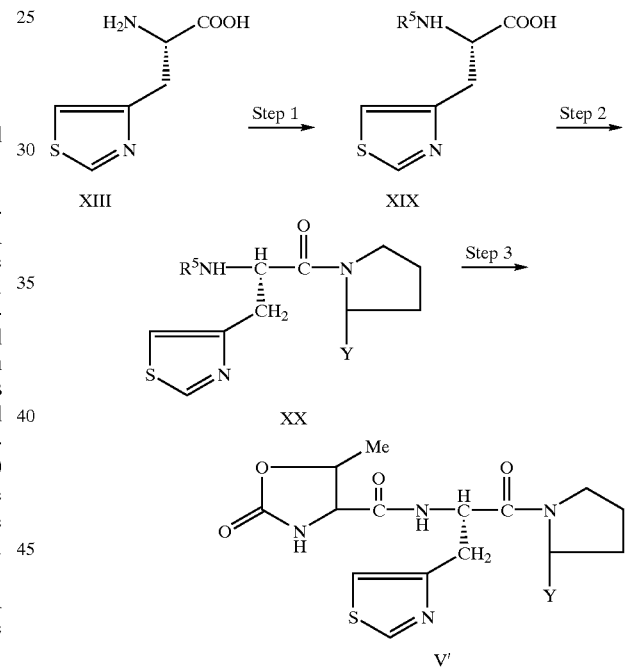

wherein R⁵ is an amino protective group and Y is as defined above.

Step 1 (Protection of an Amino Group)

The amino group of compound (XIII) synthesized in Production Examples 1 to 3 is protected by an amino protective group such as t-butyloxycarbonyl, benzyloxycarbonyl, 9-fluorenylmethoxycarbonyl, phthloyl, trifluoroacetyl, or the like (Protective Groups in Organic Synthesis, Theodora W. Green (John Wiley & Sons)). For example, when the amino group is protected by t-butyloxycarbonyl, compound (XIII) is dissolved in a solvent such as dioxane, tetrahydrofuran, acetonitrile, or the like, and Boc₂O is added to the mixture at 0 to 50° C., preferably 10 to 30° C., then the resulting mixture is stirred for 1 to 5 h, preferably 2 to 4 h. Usual after-treatment gives compound (XIX).

Step 2 (Peptide Bond Formation Reaction)

This step can be carried out in a manner similar to that described in Production Example 4 —Step 2.

Step 3 (Deprotection of $R^5$ and Peptide Bond Formation Reaction)

For example, when the amino protective group is t-butyloxycarbonyl, compound (XIX) is dissolved in a solvent such as ethyl acetate or the like, and 1 to 4N hydrochloric acid in ethyl acetate is added to the mixture at −10 to 30° C., preferably under ice-cooling, then the mixture is stirred for 1 to 5 h, preferably 2 to 3 h at the same temperature. Usual after-treatment gives the deprotected compound.

This deprotected compound is reacted in a manner similar to that described in the above peptide bond formation reaction to give compound (V').

Abbreviations described below are used in the following examples.

Ac: acetyl
Boc: tert-butyloxycarbonyl

EXAMPLE

Example 1

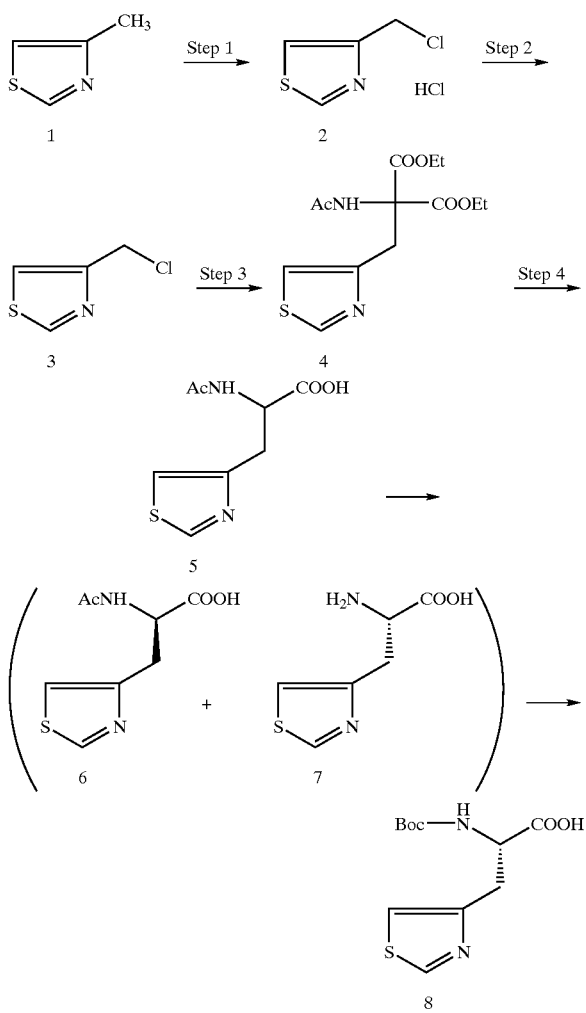

Step 1

Compound (1) (163.5 g, 1.65 mole) was dissolved in 3 L of chlorobenzene and the mixture was heated to 130° C. To the mixture was added N-chlorosuccinimide (242 g, 1.1 mole eq.) and 2,2'-azobisisobutyronitrile (13.5 g, 0.05 mole eq.). The reaction mixture was kept at the same temperature for 15 min and cooled. The mixture was poured into diluted sodium bicarbonate aq. and washed. The organic layer was separated, washed with water, and concentrated in vacuo to give 358 g of a residue including chlorobenzene. The residue was dissolved in 4 L of ethyl acetate and 260 ml of 4N hydrochloric acid in ethyl acetate (0.6 mole eq.) was added to the mixture. The precipitated crystalline was filtered to give 4-chloromethylazole hydrochloride (2) (122 g, 43.5%).

Melting point: >200° C.

$^1$H NMR (CDCl$_3$) δ ppm: 4.86(s, 2H), 7.82(d, J=2 Hz, 1H), 9.14(d, J=2 Hz, 1H), 11.22(br, 1H)

Elemental analysis (C$_4$H$_5$NSCl$_2$)

Calcd.: C;28.25%, H;2.96%, N;8.24%, S;18.85%, Cl;41.70%

Found: C;28.27%, H;2.97%, N;8.21%, S;18.72%, Cl;41.45%

Step 2

To a solution of compound (2) (154 g, 0.9 mole) in 0.5 L of water were added 3 L of toluene and sodium bicarbonate (113 g, 1.5 mole eq.). The organic layer was washed with water and the aqueous layer was extracted with toluene. The combined organic layer was dried over magnesium sulphate and concentrated in vacuo to give 124 g of 4-chloromethyltriazole (3) (including toluene (10%) Yield 93%)).

$^1$H NMR (CDCl$_3$) δ ppm: 4.76(s, 2H), 7.38(d, J=2 Hz, 1H), 8.81(d, J=2 Hz, 1H)

Step 3

To a 20% solution of sodium ethoxide in ethanol (306 g, 1.06 mole eq.) was added diethylacetoamidomalonate (96 g, 1.06 mole eq.) and the mixture was stirred for 2 h at reflux. To the reaction mixture was added a solution of compound (3) (124 g, including toluene (10%), 0.84 mole) in 0.6 L of ethanol at 50° C. and the resulting mixture was stirred for 3 h at the same temperature. The reaction mixture was cooled, poured into diluted hydrochloric acid aq., and extracted with ethyl acetate. The organic layer was washed with water, dried over sodium sulfate, and concentrated in vacuo. The residue was recrystallized from ethyl acetate/n-hexane to give compound (4) (205 g, 72.5%).

Melting point: 104–5° C.

$^1$H NMR (CDCl$_3$) δ ppm: 1.28(t, J=7.2 Hz, 6H), 1.97(s, 3H), 3.88(s, 2H), 4.30(q, J=7.2 Hz, 4H), 6.70(br, 1H), 7.20(d, J=2 Hz, 1H), 8.68(d, J=2 Hz, 1H)

Elemental analysis (Cl$_{13}$H$_{18}$N$_2$O$_5$S)

Calcd.: C;49.65%, H;5.73%, N;8.91%, S;10.18%

Found: C;49.64%, H;5.69%, N;8.88%, S;1017%

Step 4

To compound (4) (201.2 g, 0.64 mole) was added 960 ml of 3N sodium hydroxide aq. and the mixture was stirred for 1.5 h at 50° C. To the mixture was added 100 ml of conc. hydrochloric acid for adjusting the pH to 3.5 and the resulting mixture was stirred for 3 h at 100° C. keeping the pH about 4. After cooling, 120 g of acylase (Tokyo Chemical Industry Co., Ltd., Amano Pharmaceutical Co., Ltd.) was added to the mixture for adjusting the pH to 6.7 and the resulting mixture was stirred for 4 h at 37° C. The immobilized enzyme was filtered off and 500 ml of dioxane, 90.8 g of Boc$_2$O (0.6 mole eq.), and 58 ml of triethylamine (0.6 mole eq.) were added to the filtrate, which was stirred for 2 h at 25° C. Ethyl acetate (1 L) was added to the mixture, and the resulting mixture was stirred and partitioned. The aqueous phase was adjusted to the pH 3.0 and extracted with ethyl acetate. The organic phase was washed, dried over sodium sulphate, and concentrated in vacuo to give compound (8) (70 g, 40%).

Melting point: 118–119° C.

[α]$_D$=+131° (c=1.001, CHCl$_3$, 25° C.)

NMR(CDCl$_3$): 8.93(1H, d, J=2.1 Hz), 7.15(1H, d, J=2.1 Hz), 5.52(1H, d, J=5.4 Hz), 4.58(1H, m), 3.55(1H, dd, J=3.6 and 14.5 Hz), 3.40(1H, dd, J=5.4 and 14.5 Hz), 1.47(9H, s).

Elemental analysis (C$_{11}$H$_{16}$N$_2$O$_4$S)

Calcd.: C,48.32; H,5.92; N,10.29; S,11.77.

Found: C,48.07; H,5.85; N,10.17; S,11.71.

Example 2

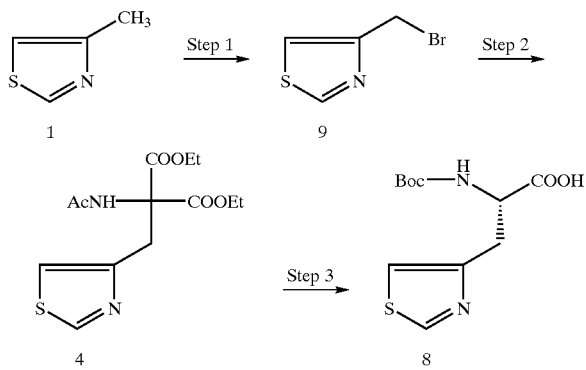

Step 1

A solution of compound (1) (4.96 g, 50 mmole) in 125 ml of carbon tetrachloride was heated at 75° C. and N-bromosuccinimide (7.57 g, 0.85 mole eq.) and 2,2'-azobisisobutyronitrile (0.41 g, 0.05 mole eq.) were added thereto. The resulting mixture was kept at the same temperature for 60 min and cooled. This reaction mixture was poured into diluted sodium bicarbonate aq. and washed. The organic layer was partitioned and washed with water. The organic layer was concentrated in vacuo to give 7.05 g of the residue (purity of compound (9) is 70%, yield 55%).

$^1$H NMR (CDCl$_3$) δ ppm: 4.65(s, 2H), 7.37(d, J=2 Hz, 1H), 8.82(d, J=2 Hz, 1H)

Step 2

To a 20% solution of sodium ethoxide in ethanol (13.6 g, 0.8 mole eq.) was added diethylacetoamidomalonate (8.69 g, 0.8 mole eq.) and the mixture was stirred for 1 h at reflux. To the reaction mixture was added a solution of compound (9) (7.05 g, 0.40 mole) in 70 mL of ethanol at 55° C. and the resulting mixture was stirred for 1.5 h at the same temperature. The reaction mixture was cooled, poured into diluted hydrochloric acid aq., and extracted with ethyl acetate. The organic layer was washed with water, dried over sodium sulfate, and concentrated in vacuo. The residue was subjected to silica gel column chromatography (toluene: ethyl acetate=4:1 to 2:1). The eluted fraction was concentrated in vacuo and recrystallized from ethyl acetate and n-hexane to give 6.30 g of compound (4) (40% yield form compound (1)).

Melting point: 104–5° C.

$^1$H NMR (CDCl$_3$) δ ppm: 1.28(t, J=7.2 Hz, 6H),1.97(s, 3H), 3.88(s, 2H), 4.30(q, J=7.2 Hz, 4H), 6.70(br, 1H), 7.20(d, J=2 Hz, 1H), 8.68(d, J=2 Hz, 1H)

Step 3

Compound (8) was synthesized in the same manner as that described in Step 4 of Example 1.

Example 3

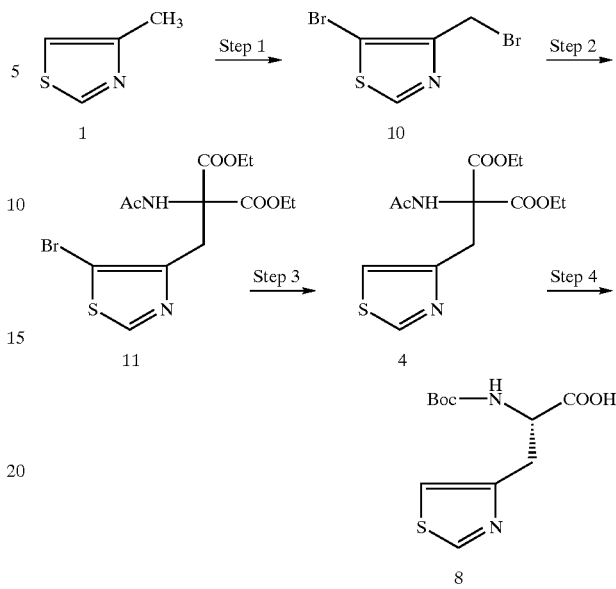

Step 1

A solution of compound (1) (4.60 g, 46.4 mmole) in 1.15 ml of carbon tetrachloride was heated at 75° C. and to this solution were added N-bromosuccinimide (20.65 g, 2.50 mole eq.) and benzoyl peroxide (2.80 g, 0.25 mole eq.). The resulting mixture was kept at the same temperature for 60 min and cooled. This reaction mixture was poured into diluted sodium bicarbonate aq. and washed. The organic layer was partitioned, washed with water, and concentrated in vacuo to give 9.65 g of a residue (purity of compound (10) is 80%, yield 53%).

$^1$H NMR (CDCl$_3$) δ ppm: 4.61(s,2H), 8.78(s, 1H)

Step 2

To a 20% solution of sodium ethoxide in ethanol (12.8 g, 1.0 mole eq.) was added diethylacetoamidomalonate (8.16 g, 1.0 mole eq.) and the mixture was stirred for 1 h at reflux. To the reaction mixture was added a solution of compound (10) (9.65 g, 37.6 mole) in 10 mL of ethanol at 55° C. and the resulting mixture was stirred for 1.5 h at the same temperature. The reaction mixture was cooled, poured into diluted hydrochloric acid aq. and extracted with ethyl acetate. The organic layer was washed with water, dried over sodium sulfate, and concentrated in vacuo. The residue was subjected to silica gel column chromatography (toluene:ethyl acetate=4:1 to 3:1). The eluting fractions were concentrated in vacuo and recrystallized from ethyl acetate and n-hexane to give 8.10 g of compound (11) (57.8% yield form compound (1)).

Melting point: 124–6° C.

$^1$H NMR (CDCl$_3$) δ ppm: 1.29(t, J=7.2 Hz, 6H), 1.99(s, 3H), 3.85(s, 2H), 4.29(q, J=7.2 Hz, 4H), 6.65(br, 1H), 8.65(d, J=2 Hz, 1H)

Elemental analysis (C$_{13}$H$_{17}$N$_2$O$_5$SBr)

Calcd.: C;39.70, H;4.36, N;7.12, S;8.15, Br;20.32

Found: C;39.68, H; 4.29, N;7.16, S;8.10, Br;20.27

Step 3

To a solution of compound (11) (1.97 g, 5 mmole) in 50 ml of methanol were added 0.20 g of 10% Pd—C and sodium acetate trihydrate (0.75 g, 1.1 mole eq.) and the mixture was hydrogenated under 4kg/cm$^2$. Pd—C was filtered off and methanol was concentrated in vacuo. The residue was dissolved in ethyl acetate and the solution was poured into diluted sodium bicarbonate aq. and partitioned. The organic layer was washed with water, dried over sodium sulfate, and concentrated in vacuo to give compound (4) (1.53 g, 97.5%).

Melting point 104–5° C.

$^1$H NMR (CDCl$_3$) δ ppm: 1.28(t, J=7.2 Hz, 6H), 1.97(s, 3H), 3.88(s, 2H), 4.30 (q, J=7.2 Hz, 4H), 6.70(br, 1H), 7.20(d, J=2 Hz, 1H), 8.68(d, J=2 Hz, 1H)

Step 4

Compound (8) was synthesized in the same manner as that described in step 4 of Example 1.

Example 4

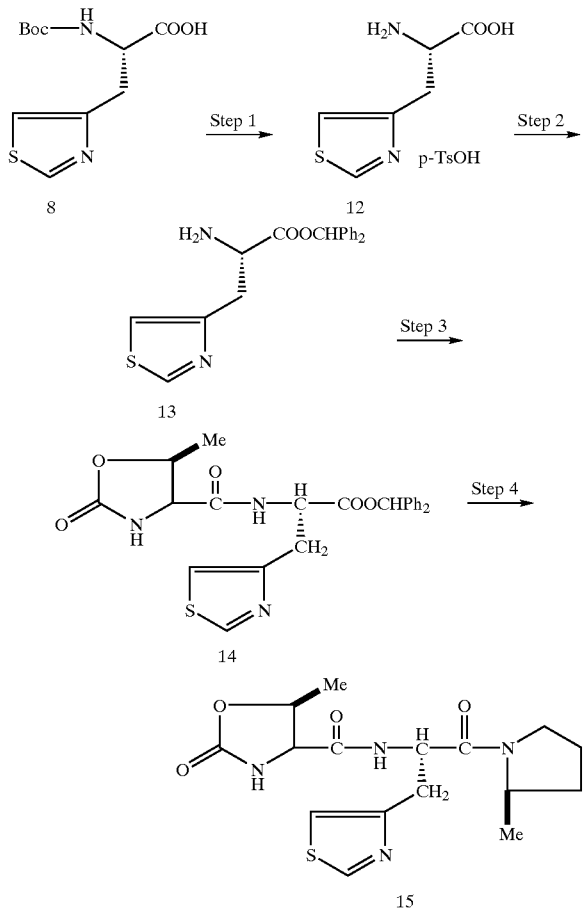

Step 1

A mixture of compound (8) (21.79 g, 80 mmol) and trifluoroacetic acid (80 ml) was stirred for 2.5 h under ice-cooling. To the mixture was added p-toluenesulfonic acid hydrate (15.22 g, 80 mmol) and the resulting mixture was stirred for 30 min at room temperature. The resulting mixture was concentrated in vacuo. To the residue were added water and methanol and the mixture was concentrated in vacuo for removing excess trifluoroacetic acid. Diethyl ether was added to the residue and the precipitated crystalline was collected by filtration to give 29.8 g (quantitative) of compound (12).

NMR(CD$_3$OD): 9.01(1H, d, J=1.8 Hz), 7.70(2H, m), 7.46(1H, d, J=1.8 Hz), 7.23(2H, m), 4.38(1H, dd, J=4.8 and 7.6 Hz), 3.45(2H, m), 2.37(3H, s).

Step 2

To a solution of compound (12) (38.85 g, 112.8 mmol) in ethanol (200 ml) and THF (600 ml) was gradually added diphenyldiazomethane (39 g, 201 mmol) with stirring at room temperature over 30 min. After the reaction mixture was stirred for 1 h at room temperature, diphenyldiazomethane (10 g, 51.5 mmol) was added and further the resulting mixture was stirred for 1 h. Acetic acid (0.1 ml) was added to the mixture to quench the excess reagent, then the mixture was concentrated in vacuo to remove the solvent. To the residue (92 g) was added diethyl ether (1 L) for crystallization, to give compound (13) (49.05 g, 96.1%).

Melting point: 139–140° C.

[α]$_D$=−34.7° (c=1.006, CHCl$_3$, 23° C.)

IR(KBr)cm$^{-1}$: 1753, 1602, 1512, 1496, 1260, 1224, 1171, 1124, 1036, 1012.

NMR(CD$_3$OD): 8.92(1H, d, J=2 Hz), 7.70(2H, m), 7.2–7.4(13H, m), 6.91(1H, s), 4.62(1H, t, J=5.8 Hz), 3.47 (2H, d, J=5.8 Hz), 2.36(3H, s).

Elemental analysis (C$_{26}$H$_{26}$N$_2$O$_5$S$_2$)

Calcd.: C,61.16; H,5.13; N,5.49; S,12.56.

Found: C,61.14; H,5.32; N,5.41; S,12.46.

Step 3

To a solution of cis-L-5-methyl-2-oxo-oxazolidine-4-carboxylic acid (13.95 g, 96.14 mmol), compound (13) (49.09 g, 96.14 mmol), N-hydroxybenzotriazole (2.6 g, 19.23 mmol), and triethylamine (14.1 ml, 101 mmol) in 1 L of THF was added DCC (20.83 g, 101 mmol) under ice-cooling. After stirring for 10 min at the same temperature, the ice bath was removed and the mixture was further stirred for 20 min at the room temperature. After the precipitate was filtered off, the filtrate was concentrated in vacuo to give an oily residue (82.7 g). The oily residue was dissolved in 700 ml of ethyl acetate with heating and the insoluble residue was filtered off. The filtrate was washed with sodium carbonate aq. and water. Methanol (20 ml) was added to the organic phase and the mixture was dried over magnesium sulphate and concentrated in vacuo. The precipitated crystalline was collected by filtration and washed with a mixed solvent of ethyl acetate and diethyl ether (2:3) to give compound (14) (35.69 g, 79.8%).

After the mother liquor was concentrated in vacuo, the residue was crystallized from a mixed solvent of ethyl acetate and diethyl ether to give compound (14) (2.62 g, 5.9%).

Melting point: 176–177° C.

[α]$_D$=−39.2° (c=1.007, CHCl$_3$, 24° C.)

IR(KBr)cm$^{-1}$: 1739, 1681, 1508, 1453, 1386, 1237, 1193, 1089.

NMR(CDCl$_3$): 8.71(1H, d, J=1.8 Hz), 8.18(1H, d, J=7.8 Hz), 7.2–7.4(10H, m), 6.82(1H, s), 6.66(1H, d, J=1.8 Hz), 5.79(1H, s), 5.12(1H, m), 4.94(1H, m), 4.35(1H, dd, J=1.8 and 9.0 Hz), 3.40(1H, dd, J=5.7 and 15 Hz), 3.29(1H, dd, J=4.5 and 15 Hz), 1.27(3H, d, J=6.3 Hz).

Elemental analysis (C$_{24}$H$_{23}$N$_3$O$_5$S)

Calcd.: C,61.92; H,4.98; N,9.03; S,6.89.

Found: C,61.95; H,5.01; N,8.94; S,6.62.

Step 4–1

To compound (14) (41.24 g, 88.59 mmol) were added anisole (240 ml) and trifluoroacetic acid (120 ml) under ice-cooling and the mixture was stirred for 15 min. After the ice bathe was removed, the mixture was stirred for 2.5 h at room temperature. The reaction mixture was concentrated in vacuo, and 500 ml of diethyl ether was added to the oily residue, then the precipitated powder was collected. The powder was dissolved in a mixed solvent of water (50 ml) and methanol (300 ml) and the insoluble residue was filtered off. The filtrate was concentrated in vacuo to a small amount, to which a seed crystal and methanol were added, and the mixture was allowed to stand for 3 days at room temperature. The precipitated crystal was collected by filtration to give the deprotected compound (14.89 g, 56.1%). The mother liquor was concentrated in vacuo, which was crystallized again from methanol and diethyl ether to further give a deprotected compound (10.3 g, 38%).

Melting point: 214–215° C.
$[\alpha]_D = -4.2°$ (c=0.5, H$_2$O, 22° C.)
IR(Kbr)cm$^{-1}$: 1753, 1707, 1655, 1548, 1529, 1409, 1343, 1264, 1236, 1102, 1092.
NMR(DMSO-d$_6$): 9.02(1H, d, J=1.8 Hz), 8.46(1H, d, J=7.8 Hz), 7.74(1H, s), 7.38(1H, d, J=1.8 Hz), 4.77(1H, dq, J=6.6 and 8.7 Hz), 4.66(1H, m), 4.21(1H, d, J=8.7 Hz), 3.24(1H, dd, J=5.1 and 15 Hz), 3.13(1H, dd, J=8.4 and 15 Hz), 1.13(3H, d, J=6.6 Hz).
Elemental analysis (C$_{11}$H$_{13}$N$_3$O$_5$S)
Calcd.: C,44.14; H,4.38; N,14.04; S,10.71.
Found: C,43.94; H,4.478; N,14.09; S,10.58.

Step 4–2A

To a suspension of the deprotected compound (12.1 g, 40.48 mmol) and N-hydroxysuccinimide (4.66 g, 40.48 mmol) in 242 ml of THF was added DCC (8.35 g, 40.48 mM) under ice-cooling and the mixture was stirred for 30 min. After the ice bath was removed, the mixture was stirred for 2 h at room temperature. The solution of N-hydrosuccinimide ester of the deprotected compound was added to a suspension of (R)-(+)-2-methylpyrrolidine hydrochloride (5.42 g) synthesized in a manner similar to that described in Tetrahedron, 27, 2599 (1971) and triethylamine (8.46 ml, 60.72 mmol) in 121 ml of THF at the room temperature. The reaction mixture was stirred for 15 h. After the insoluble precipitate was filtered off, the filtrate was concentrated in vacuo. The residue (24.6 g) was dissolved in water (150 ml) and the precipitate was filtered off. The filtrate was subjected to gel filtration column chromatography (MCI Gel CHP 20P 600 ml) and the fractions eluted with methanol containing 40% water were collected to yield 8.87 g of crude compound (15). The crude compound (15) was subjected to silica gel column chromatography (mixed solvent of chloroform and methanol) and lyophilized to give compound (15) (5.37 g, 35.7%).

Melting point: 192–194° C.
$[\alpha]_D = -1.9$ (c=1.005, H$_2$O, 25° C.)
IR(KBr)cm$^{-1}$: 1755, 1675, 1625, 1541, 1516, 1448, 1232, 1097.
NMR(CD$_3$OD): 8.97(1H, t, J=2.1 Hz), 7.34(1H, t, J=2.1 Hz), 5.19 and 5.04(total 1H, each t, J=7.5 Hz), 4.92(1H, dq, J=6.6 and 8.7 Hz), 4.36 and 4.35(1H, d, J=8.7 Hz), 4.07 and 3.92(total 1H, each m), 3.78(1H, m), 3.42(1H, m), 3.22(2H, m), 1.5–2.0(4H, m) 1.28 and 1.22(total 3H, each d, J=6.6 Hz), 1.21 and 1.02(total 3H, each d, J=6.6 Hz).
Elemental analysis (C$_{16}$H$_{22}$N$_4$O$_4$S H$_2$O)
Calcd.: C,49.99; H,6.29; N,14.57; S,8.34.
Found: C,49.99; H,6.29; N,14.79; S,8.36.

Step 4–2B

To a solution of the deprotected compound (10 g, 33.41 mmol) and N-hydroxysuccinimide (4.04 g, 35.08 mmol) in a mixed solvent of DMF (45 ml) and THF (360 ml) was added DCC (7.24 g, 35.08 mmol) under ice-cooling and the mixture was stirred for 4 h. To the reaction mixture were added a solution of (R)-(+)-2-methylpyrrolidine p-toluensulfonate (8.6 g) which is synthesized in a manner similar to that described in Helv. Chim. Acta, 34, 2202 (1951) and triethylamine (9.32 ml, 66.82 mmol) in 11 ml of THF under ice cooling and the mixture was stirred for 4 h. After the ice bath was removed, the reaction mixture was stirred for 48 h. The insoluble precipitate was filtered off and the filtrate was concentrated in vacuo. The residue (38 g) was dissolved in 220 ml of water and the insoluble participate was filtered off. The filtrate was subjected to gel filtration column chromatography (MCI Gel CHP 20P 600 ml) and the fractions eluted with methanol containing 40% water were collected and crystallized from water to yield compound (15) (6.94 g, 56.7%) which was the same as that synthesized by method A.

Industrial Applicability

Using this process, a 4-thiazolylalanine derivative is able to be synthesized economically and in a large scale.

What is claimed is:

1. A process for the production of a compound represented by the formula (I):

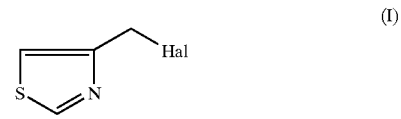

wherein Hal is halogen, which comprises reacting 4-methylthiazole with N-halosuccinimide in a solvent in the presence of 2,2-azobisisobutyronitrile, wherein Hal is the same halogen as in N-halosuccinimide.

2. A process for the production of a compound represented by the formula (III):

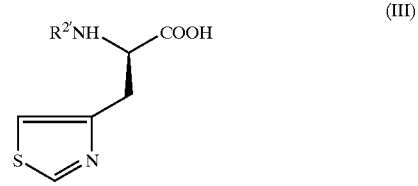

wherein R$^{2'}$ is hydrogen or an amino protective group, or the formula (IV):

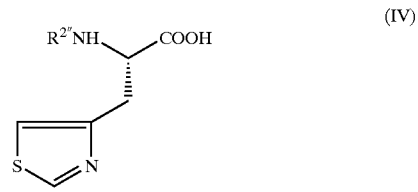

wherein R$^{2''}$ is different from R$^{2'}$ and hydrogen or an amino protective group, which comprises, (a) preparing a compound represented by the formula (I):

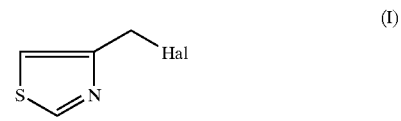

wherein Hal is halogen through the process according to claim 1, (b) preparing a compound represented by the formula (II):

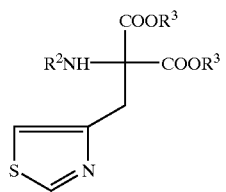

(II)

wherein $R^2$ is an amino protective group, and $R^3$ is lower alkyl, by reacting a compound represented by the formula (I) with $R^2NHCH(COOR^3)_2$, wherein $R^2$ and $R^3$ are as defined above, in the presence of a base, (c) preparing a compound represented by the formula (III) or (IV) by subjecting the compound represented by the formula (II) to hydrolysis, decarboxylation, and optical resolution.

3. A process for the production of a compound represented by the formula (V):

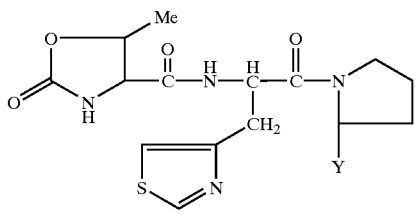

(V)

wherein Y is optionally substituted alkyl, which comprises preparing a compound represented by the formula (III) or (IV) through the process according to claim 2 and reacting a compound represented by the formula (III) or (IV) by a peptide bond formation reaction.

4. A process of claim 1 wherein the solvent is chlorobenzene and N-halosuccinimide is N-chlorosuccinimide.

5. A process of claim 1 wherein the solvent is carbon tetrachloride and N-halosuccinimide is N-bromosuccinimide.

6. A process of claim 1 wherein the solvent is trifluoromethylbenzene and N-halosuccinimide is N-bromosuccinimide.

7. A process for the production of 4-chloromethylthiazole comprising, (a) reacting 4-methylthiazole with N-chlorosuccinimide in chlorobenzene in the presence of 2,2-azobisisobutyronitrile and (b) treating the compound obtained in the step (a) with hydrochloric acid to give the corresponding hydrochloride, followed by desalting.

8. A process of claim 2 wherein the solvent is chlorobenzene and N-halosuccinimide is N-chlorosuccinimide.

9. A process of claim 3 wherein the solvent is chlorobenzene and N-halosuccinimide is N-chlorosuccinimide.

10. A process of claim 2 wherein the solvent is carbon tetrachloride and N-halosuccinimide is N-bromosuccinimide.

11. A process of claim 3 wherein the solvent is carbon tetrachloride and N-halosuccinimide is N-bromosuccinimide.

12. A process of claim 2 wherein the solvent is trifluoromethylbenzene and N-halosuccinimide is N-bromosuccinimide.

13. A process of claim 3 wherein the solvent is trifluoromethylbenzene and N-halosuccinimide is N-bromosuccinimide.

14. A process of claim 1 wherein the solvent is trifluoromethylbenzene and N-halosuccinimide is N-bromosuccinimide.

* * * * *